United States Patent
Delogé et al.

(10) Patent No.: US 7,520,902 B2
(45) Date of Patent: Apr. 21, 2009

(54) PROSTHETIC FEMORAL JOINT

(75) Inventors: Nicolas Delogé, Douvres-la-Deliverande (FR); Arnaud Auxepaules, Saint-Aubin-sur-Mer (FR)

(73) Assignee: Benoist Girard SAS (FR)

( * ) Notice: Subject to any disclaimer, the term of this patent is extended or adjusted under 35 U.S.C. 154(b) by 355 days.

(21) Appl. No.: 11/089,285

(22) Filed: Mar. 24, 2005

(65) Prior Publication Data

US 2005/0228502 A1  Oct. 13, 2005

(30) Foreign Application Priority Data

Apr. 2, 2004 (GB) ................. 0407624.6

(51) Int. Cl.
*A61F 2/32* (2006.01)
(52) U.S. Cl. ................... 623/22.15
(58) Field of Classification Search .............. 623/22.15
See application file for complete search history.

(56) References Cited

U.S. PATENT DOCUMENTS

| | | | |
|---|---|---|---|
| 3,003,399 A | | 10/1961 | Donner |
| 3,922,726 A | * | 12/1975 | Trentani et al. .......... 623/22.15 |
| 4,001,897 A | | 1/1977 | Rambert et al. |
| 4,172,296 A | | 10/1979 | D'Errico |
| 4,437,193 A | * | 3/1984 | Oh ........................ 623/22.24 |
| 4,798,610 A | | 1/1989 | Averill et al. |
| 5,062,853 A | | 11/1991 | Forte |
| 5,176,711 A | * | 1/1993 | Grimes .................... 623/22.22 |
| 5,507,824 A | * | 4/1996 | Lennox ................... 623/22.25 |

(Continued)

FOREIGN PATENT DOCUMENTS

FR  2 437 199  9/1978

(Continued)

OTHER PUBLICATIONS

Biomet Orthopedics, Inc., Freedom Constrained Liner, product information, © 2003.

(Continued)

*Primary Examiner*—Suzette J Gherbi
(74) *Attorney, Agent, or Firm*—Lerner, David, Littenberg, Krumholz & Mentlik, LLP

(57) ABSTRACT

A prosthetic hip joint replacement system has a femoral component with a tapered trunion thereon. A modular head with a part-spherical outer surface terminating in a planar surface, engages the trunion. An acetabular cup member is provided for receiving the part-spherical head of a femoral implant, the cup member has a cavity having a part-spherical inner surface for receiving the modular head. The part-spherical inner surface of the cup defines a polar axis and an equator centered about a pole of the cavity. The cavity has a part-circular opening spaced from the pole a greater distance than the equator. Thus the inner part-spherical bearing surface extends beyond the 180° which the equator extends. The configuration of the part-spherical inner bearing surface causes a movement of translation of the head during rotation so that there is a crescent shaped retention area on each opposed side thereof. The opening has a non-circular or planar portion alignable with the planar head surface during insertion of the head in the cavity and a plane parallel to the non-circular portion through the center of the portion of the opening being offset from a parallel plane containing the polar axis of the cavity.

16 Claims, 4 Drawing Sheets

U.S. PATENT DOCUMENTS

| | | | |
|---|---|---|---|
| 5,830,215 A | 11/1998 | Incavo et al. | |
| 6,187,012 B1 | 2/2001 | Masini | |
| 6,231,612 B1 * | 5/2001 | Balay et al. | 623/22.31 |
| 6,361,566 B1 * | 3/2002 | Al-Hafez | 623/22.15 |
| 6,368,352 B1 * | 4/2002 | Camino et al. | 623/19.12 |
| 6,520,995 B2 * | 2/2003 | Church | 623/22.24 |
| 6,537,321 B1 * | 3/2003 | Horber | 623/22.22 |
| 6,565,575 B2 | 5/2003 | Lewis | |
| 6,942,699 B2 * | 9/2005 | Stone et al. | 623/19.14 |
| 7,455,694 B2 * | 11/2008 | Epaules et al. | 623/22.15 |
| 2001/0032021 A1 * | 10/2001 | McKinnon | 623/22.28 |
| 2002/0116068 A1 * | 8/2002 | McLean | 623/22.15 |
| 2003/0171817 A1 | 9/2003 | Rambert et al. | |
| 2004/0143341 A1 | 7/2004 | McLean | |
| 2005/0060040 A1 * | 3/2005 | Auxepaules et al. | 623/22.18 |
| 2007/0191961 A1 * | 8/2007 | Aux Epaules et al. | 623/22.18 |
| 2008/0114459 A1 * | 5/2008 | Scott et al. | 623/18.11 |

FOREIGN PATENT DOCUMENTS

| | | |
|---|---|---|
| FR | 2 676 260 | 5/1991 |
| FR | 2 785 525 | 11/1998 |
| FR | 2 795 302 | 6/1999 |
| FR | 2 807 315 | 4/2000 |
| WO | WO-01/76511 A | 10/2001 |
| WO | WO-02/058597 A | 8/2002 |

OTHER PUBLICATIONS

N. Deloge, Dual Mobility Cup, Stryker Orthopaedics, Jul. 20, 2004.

N. Deloge, Dual Mobility Cup, Stryker Orthopaedics.

* cited by examiner

PROSTHETIC FEMORAL JOINT

BACKGROUND OF THE INVENTION

This invention relates to a prosthetic femoral joint which comprises a part-spherical cup adapted for location in an acetabulum and having a part-spherical inner bearing surface to receive a part-spherical ball head which can be attached to a stem for location in a femur and in which the inner bearing surface of the cup extends around an angle of more than 180°. Cups of this type are known which comprise a single element made, for example, of a synthetic plastics material or metal. The inner bearing surface can also be formed on an insert which again can be of a synthetic plastics material, a ceramic, or a metal and which is carried in an outer housing or shell, the housing engaging the acetabulum with which it is to be used and being held in place by, for example, cement or by mechanical means, for example nails or screws. The cup is used in connection with Total Hip Arthroplasty which includes implanting a femoral component in the femur which component normally includes the ball head.

In other known constructions of the cup the inner bearing surface can be provided on an inner layer or insert made from a different material from an outer backing which engages the acetabulum. Dual mobility cups or bipolar cups generally comprise an inner bearing surface which receives the part-spherical ball head and which is itself freely rotably mounted in a part-spherical element which has outer and inner bearing surfaces. The outer bearing surface engages the inner bearing surface of an outer housing which engages the acetabulum. This type of cup allows greater mobility of angular movement. Such cups are shown in U.S. Pat. No. 4,798,610 and U.S. Publication No. 2004/0143341.

In all these constructions, and, more especially, dual mobility cups, it is advantageous to have a means for retaining the ball head against the inner bearing surface. There are various ways of achieving this with a hard material and at least two ways of retaining the ball head inside the inner bearing surface. For example, U.S. Pat. No. 4,798,610 uses a ring seated on a conically tapered surface in the inner bearing. A deformable material cannot be used and in a first arrangement a ring or circlip is used but this requires a third part and there is risk of wear. The second arrangement can consist of having two flats on the head and turning the head at 90° prior to inserting it into the cup and then again turning the head back through 90°. A disadvantage with this type of construction is that specific heads are required and there is the risk of wear due to the truncating of the head. A system of this type is shown in FR 2 785 525 and FR 2 807 315.

The present invention is intended to overcome some of the disadvantages referred to above.

SUMMARY OF THE INVENTION

According to the present invention a prosthetic femoral joint comprises a part-spherical cup adapted for location in an acetabulum having a part-spherical inner bearing surface to receive a part-spherical ball head which can be attached to a stem for location in a femur. The part-spherical inner bearing surface of the cup extends around an angle of more than 180°, and a portion thereof adjacent an entry mouth is formed with a substantially flat face which is at a radius from the center of the part-spherical inner bearing surface. This radius is less than the radius of the remainder of the cup, and the ball head has a co-operating substantially flat face on its part-spherical surface on which is provided a structure to receive and retain the stem with which it is to be used, and which prior to attachment to the stem allows it to be located in the cup and rotated so that it is retained thereon. The dimensions and configuration of the part-spherical inner bearing surface and the part-spherical bearing surface on the ball head being arranged to cause a movement of translation of the head during rotation to displace the head so that there is a crescent shaped retention area on each opposed side thereof.

An advantage of this construction is that some standard sized ball heads can be used. The entry into the cup can be closely controlled by the dimensions of the flat on the inner bearing surface so that the operation of the ball head against the bearing surface is accurate.

In a preferred construction the transverse axis of the mouth of the cup which is substantially parallel with the flat face of the ball head when being inserted is offset from the transverse axis of the inner bearing surface of the cup. The offset can be less than 10 mm, for example up to 5 mm.

The invention can be applied to cups and balls of any suitable material, for example synthetic plastics material, metals or ceramics.

An amount, for example, 1 mm of free subluxation can be incorporated if necessary.

The invention can also be applied to cups in which the inner bearing surface is provided on an inner bearing layer or to dual mobility cups in which the inner bearing layer is formed as an insert which can move within another bearing layer within a backing and to cemented or non-cemented cups.

In the present invention a prosthetic hip replacement system comprises a femoral component having a trunion or spigot thereon which receives a modular head with a part-spherical outer surface terminating in a planar surface which planar surface has an axial bore for engaging the trunion of the femoral component. An acetabular cup which may have an outer shell and an inner bearing member for receiving the part-spherical head of the femoral implant is also provided. The bearing member has a cavity with a part-spherical inner surface for receiving the modular head, the part-spherical inner surface defining a polar axis and an equator oriented 90° from a pole of the cavity. The cavity has a part-circular opening for receiving the head which opening is spaced from the pole an axial distance greater than an axial distance to the equator. The opening has a circular and a non-circular portion, the non-circular portion alignable with the planar head portion during insertion of the head into the cavity in the bearing. A plane extending parallel to the non-circular opening portion through a center of the circular opening portion being offset from a parallel plane containing the polar axis of the cavity. The offset is preferably in a direction away from the non-circular opening portion.

In the preferred embodiment, the offset is less than 10 mm and more preferably between 5 and 10 mm. Preferably, the opening is in the form of a generally "D" shape wherein the non-circular portion has two linear portions separated by a curved portion. Of course, the linear portion of the "D" may be planar without the curved portion. The design can be used in a standard acetabular cup or in a bipolar cup in which the bearing element rotates on the inner surface of the shell.

BRIEF DESCRIPTION OF THE DRAWINGS

The invention can be performed in various ways and some embodiments will now be described by way of example and with reference to the accompanying drawings in which.

DETAILED DESCRIPTION

Figure 1:
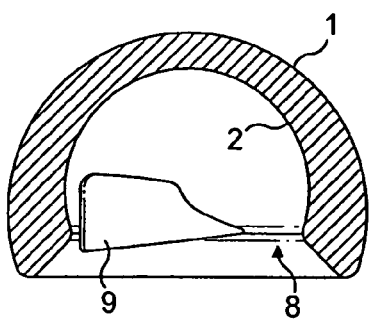
FIG. 1 is a diagrammatic cross-sectional side elevation of a part-spherical acetabular cup embodying the invention.
Figure 2:
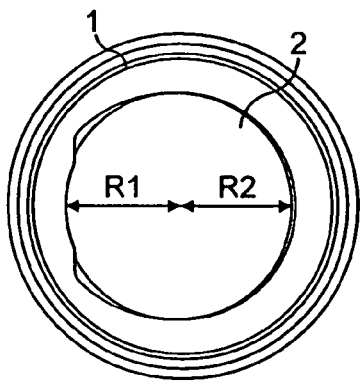
FIG. 2 is a plan view of the cup shown in FIG. 1.
Figure 8:
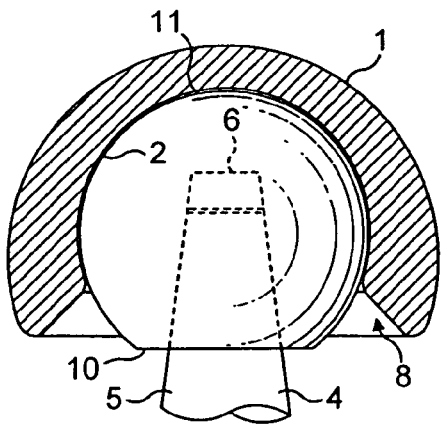
FIG. 8 shows the ball head connected to the stem.

FIGS. 1 and 2 show the application of the invention to a prosthetic femoral joint which comprises a part-spherical cup 1 which is made from a single material, for example a synthetic plastics material such as ultra-high molecular weight polyethylene, and which is adapted for location in an acetabulum. The cup 1 has a part-spherical inner bearing surface 2 to receive a part-spherical ball head 3 (see FIG. 5) which can be attached to a stem 4 (see FIG. 8) for location in a femur. The stem 4 has a shoulder carrying a tapered spigot 5 which is adapted to locate and be retained in a tapered socket 6. This method of attachment is well-known and the construction of the stem and spigot are also well-known in themselves and will not be described further.

As will be seen from FIG. 1, the inner bearing surface 2 of the cup extends around an angle of more than 180° i.e. below the equator and a portion thereof adjacent an entry mouth 8 is formed with a substantially flat face 9 which is at a radius R1 from the centre of the hemispherical inner bearing surface 2 which is less than the radius R2 of the remainder of the cup.

Figure 5:
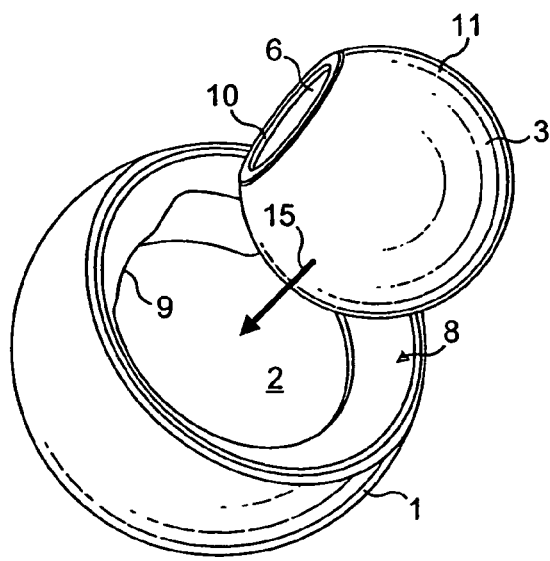
FIG. 5 is a diagrammatic exploded view showing how an unattached ball head is inserted into the cup with which it is to be used.

As shown in FIG. 5, the ball head 3 has a co-operating substantially flat face 10 on its spherical surface 11 and which, prior to attachment of a ball head to the spigot 5 of the stem 4, allows it to be located in the cup and then be rotated so that it is retained therein.

It will be seen that the tapered opening 6 extends inwardly into the ball head from the flat face 10 so that it is substantially outside the bearing surfaces of the cup and the ball to provide the greatest possible bearing area between them.

Figure 6:
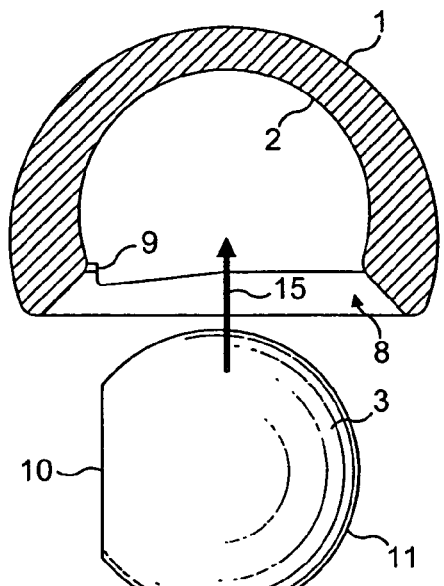
FIG. 6 is a cross-sectional diagrammatic side elevation again showing how the ball head is inserted.
Figure 7:
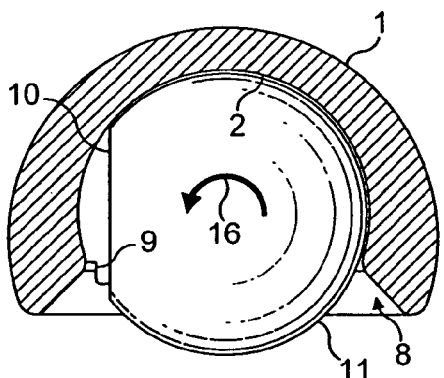
FIG. 7 shows the ball head in place in the cup.

FIGS. 5, 6, 7 and 8 show the sequence of assembling the ball head 3 into the cup 1. As shown in FIG. 6, the ball is rotated so that the flat face 10 aligns with the flat face 9 of the cup. The direction of insertion is indicated by arrow 15. The ball head is moved into the cup until it reaches the position shown in FIG. 7. It is now rotated in the direction of the arrow 16 until it reaches the position shown in FIG. 8. The ball is now retained in the cup and the spigot 5 of the stem 4 is locked into position in the tapered opening 6. (In order to clarify the drawings the tapered spigot 5 and tapered opening 6 are not shown in FIGS. 6 and 7).

Figure 9:
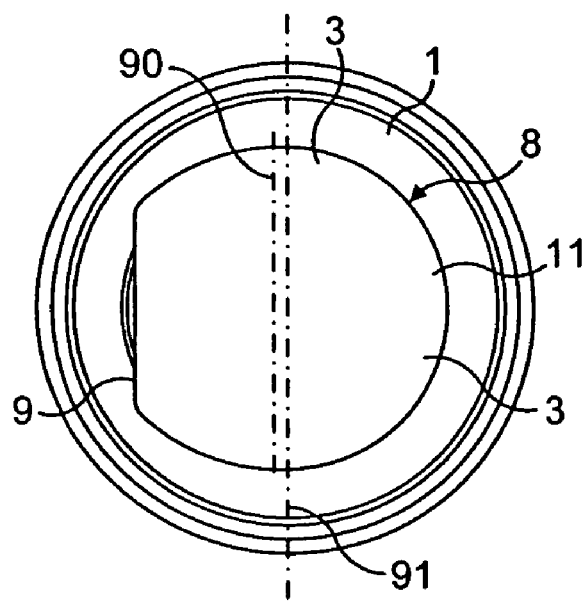
FIG. 9 is a plan view of a cup showing the ball head during entry and in which the construction allows a slight movement of translation.

There is a slight movement of translation of the head during the rotation to slightly displace the head so that there is a crescent shaped retention area on each side. As shown in FIG. 9 the transverse axis 90 of the mouth or opening 8 of the cup, which axis 90 is substantially parallel with the flat face 9, is offset by up to 5 mm from the transverse axis indicated by reference numeral 91 of the part-spherical surface 2 of the cup. Thus, upon insertion, the transverse axis of ball 3 is aligned with the axis 90 so that the ball enters the cup slightly offset to the left as shown in FIG. 9. When the ball is rotated and in place on the inner bearing surface 2 of the cup 8 there is a translational movement of the ball to the position shown in FIG. 10 where it will be seen that the axis 90a of the ball is now in line with the main axis 91 of the cup.

Figure 10:
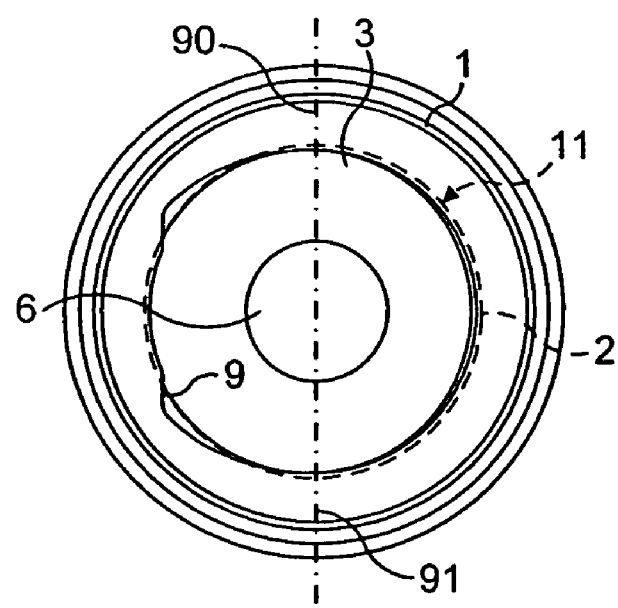
FIG. 10 is a similar view to FIG. 9 showing the ball head in position in the cup.
Figure 11:
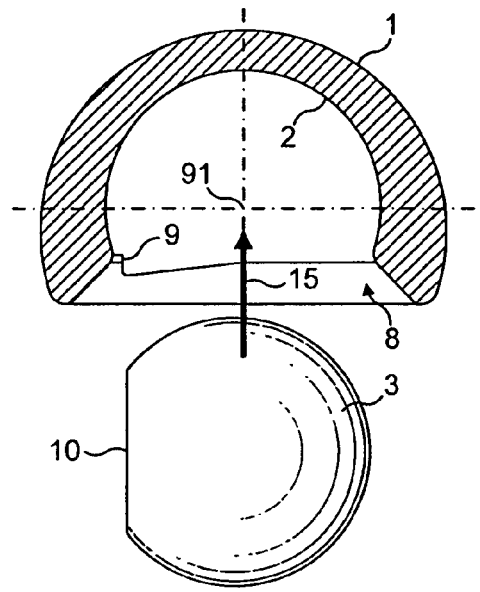
FIGS. 11 to 15 show the sequence of fitting the ball into the cup showing the movement of translation of the head during the rotation.
Figure 12:
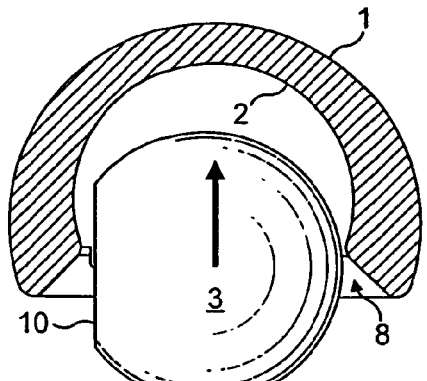
Figure 13:
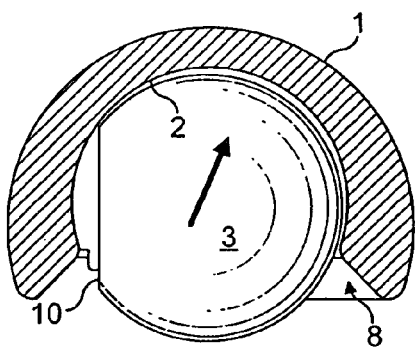
Figure 14:
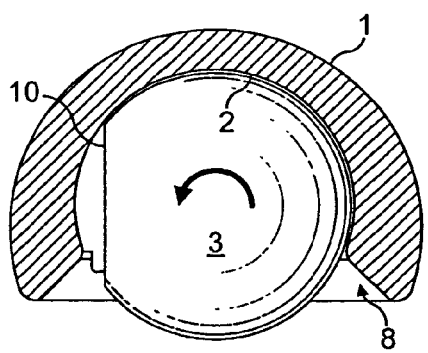
Figure 15:
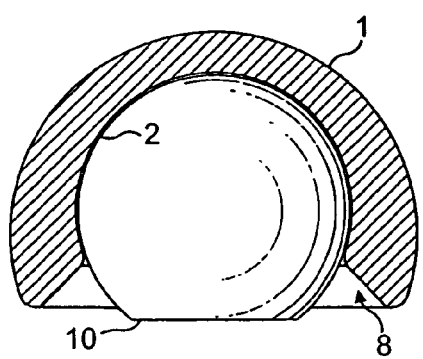

FIGS. 11 to 15 show the sequence of inserting the ball head 3 of FIGS. 9 and 10 into a cup 1. As will be seen the ball head is inserted, as shown in FIG. 12, and is moved to the right to provide the movement of translation. With the ball in this position it is rotated, as indicated by the arrow in FIG. 14, and is finally held in position as shown in FIG. 15.

This type of construction could also be employed in FIGS. 3 and 4 described below.

The slight movement of translation enables the retention of the head on the left and right sides.

The trunion or spigot 5 can be locked into the ball head 3 at any time during the surgical proceedings, for example the ball could be locked into the cup prior to assembly into the acetabulum, during assembly thereto, or after the cup has been cemented or held in position by any other means.

Figure 3:
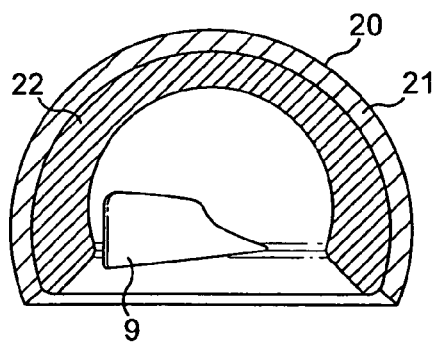
FIG. 3 is a diagrammatic cross-sectional side elevation of an alternative form of cup which has a backing.

FIG. 3 shows how the invention can be applied to a cup using a liner in a backing and the same reference numerals are used to indicate similar parts to those used in the other FIGS. In this construction the cup 20 comprises an outer backing 21 made from metal or synthetic plastics material or any other suitable material and is provided with a liner 22 again made from any suitable material. The construction of the liner is similar to the construction of the cup shown in FIGS. 1 and 2 and the invention is applied in the same way.

Figure 4:
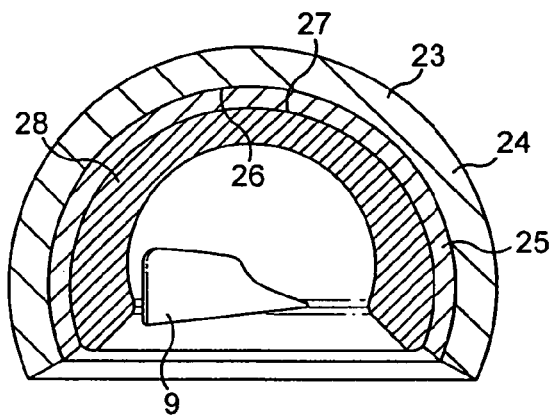
FIG. 4 is a diagrammatic cross-sectional view of another alternative construction using a dual mobility cup.

FIG. 4 shows how the invention can be applied to a dual mobility (bipolar) cup 23. Again the same reference numerals are used to indicate similar parts as the previous constructions but with this arrangement the cup comprises an outer backing 24, an inner movable member 25 which has an outer bearing surface 26 and an inner bearing surface 27 and in which is retained a bearing insert 28 the general construction of which is similar to the construction shown in FIGS. 1 and 2. This type of dual mobility cup provides a greater range of movement for the joint.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic hip joint replacement system comprising:
a femoral component having a trunion thereon;
a modular head with a part-spherical outer surface terminating in a planar surface, said planar surface having an axial bore for engaging the trunion on the femoral component;
an acetabular cup member for receiving the part-spherical head of a femoral implant, the cup member comprising,
a cavity having a hemi-spherical inner bearing surface for receiving the modular head, said hemi-spherical inner surface defining a polar axis perpendicular to a plane of an equator spaced from a proximal pole of the cavity, said cavity having a part-circular opening for receiving said modular head, the opening lying in a plane parallel to the plane of the equator and spaced an axial distance from said proximal pole a greater distance than the plane containing said equator, said opening having a circular portion and a non-circular portion, the non-circular portion of the opening alignable with the planar head portion during insertion of the head into the cavity and a plane perpendicular to the equator through a center of the circular portion forming said part-circular opening being offset from a parallel plane containing said polar axis of the hemi-spherical inner surface of the cavity.

2. The prosthetic hip joint as set forth in claim 1 wherein the offset is from 5 m to 10 mm.

3. The prosthetic hip joint as set forth in claim 1 wherein the inner surface of the cavity is shaped to cooperate with the head as the femoral component articulates relative to the acetabular cup.

4. The prosthetic hip joint as set forth in claim 1 wherein the opening is in the form of a generally D-shaped opening.

5. The prosthetic hip joint as set forth in claim 1 wherein the non-circular portion has two linear portions separated by a curved portion.

6. The prosthetic hip joint as set forth in claim 1 wherein the head is metal.

7. The prosthetic hip joint as set forth in claim 1 wherein the head is ceramic.

8. The prosthetic hip joint as set forth in claim 1 wherein the acetabular cup member is a polyethylene bearing.

9. A prosthetic femoral joint comprising a part-spherical cup adapted for location in an acetabulum and having a hemi-spherical inner bearing surface having an opening to receive a part-spherical ball head which can be attached to a stem for location in a femur, the opening lying in a plane perpendicular to a polar axis through a pole of the part-spherical inner bearing surface and in which the part-spherical inner bearing surface of the cup extends beyond a plane of an equator to a latitude with respect to the proximal pole of the hemi-spherical inner bearing, the equator plane being parallel to the opening plane and a portion of the opening forming a part-circular entry mouth with a substantially flat face which is at a radius from a center of the part-circular entry mouth which is less than the radius of the remainder of the part-circular entry mouth, and in which the ball head has a co-operating substantially flat face on its part-spherical surface on which is provided means to receive and retain the stem with which it is to be used, an axis through the center of the part-circular entry mouth parallel to the polar axis being offset from the polar axis of the hemi-spherical inner bearing surface towards the flat face of the entry mouth and which entry mouth prior to attaching the ball head to said stem allows the ball head to be located in the cup and rotated so that it is retained thereon, the dimensions and configuration of the hemi-spherical inner bearing surface and a part-spherical bearing surface of the ball head being arranged to cause a movement of translation of the head during rotation to displace a polar axis of the head from the center of the part-circular portion of the entry mouth toward the polar axis of the hemi-spherical inner bearing surface so that there is a crescent shaped retention area on each opposed side thereof.

10. The prosthetic femoral joint as claimed in claim 9 in which the center axis of the mouth of the cup is on a plane substantially parallel with the flat face of the ball head when being inserted is offset from a plane containing the polar axis of the inner bearing surface of the cup.

11. The prosthetic femoral joint as claimed in claim 10 in which the offset is less than 10 mm.

12. The prosthetic femoral joint as claimed in claim 11 wherein the offset is between 5 and 10 mm.

13. The prosthetic femoral joint as claimed in claim 9 in which the inner bearing surface of the cup is provided on an inner bearing layer.

14. The prosthetic femoral joint as claimed in claim 13 in which the inner bearing layer is formed as an insert which can move within another bearing layer within a backing to provide a dual mobility cup.

15. The prosthetic femoral joint as claimed in claim 9 in which the cup is adapted for location in an acetabulum with cement.

16. The prosthetic femoral joint as claimed in claim 9 in which the cup is adapted to be located in an acetabulum without cement.

* * * * *